United States Patent [19]

Powers et al.

[11] Patent Number: 5,224,485
[45] Date of Patent: Jul. 6, 1993

[54] PORTABLE DATA ACQUISITION UNIT

[75] Inventors: Daniel J. Powers; Jeffrey C. Osborne; Peter M. Galen; Susan R. Hart; William E. Saltzstein, all of McMinnville, Oreg.

[73] Assignee: Hewlett-Packard Company, Palo Alto, Calif.

[21] Appl. No.: 706,139

[22] Filed: May 28, 1991

[51] Int. Cl.$^5$ ............................................. A61B 5/04
[52] U.S. Cl. .................................................... 128/696
[58] Field of Search ............... 128/696, 710, 709, 903; 364/413.06; 340/870.13, 825.06; 370/112

[56] References Cited

U.S. PATENT DOCUMENTS

| 3,380,228 | 8/1967 | Foner . | |
| 3,757,778 | 9/1973 | Graham . | |
| 4,146,750 | 3/1979 | Spiesman | 340/870.13 |
| 4,249,538 | 2/1981 | Musha et al. | 364/413.06 |
| 4,296,464 | 10/1981 | Woods et al. | 364/200 |
| 4,883,064 | 11/1989 | Olson et al. | 128/696 |
| 5,086,778 | 2/1992 | Mueller et al. | 364/413.06 |
| 5,113,523 | 5/1992 | Colley et al. | 364/136 |

Primary Examiner—Lee S. Cohen
Assistant Examiner—Samuel Gilbert

[57] ABSTRACT

A portable data acquisition unit which features a sample order register which sets addresses in a multiplexer unit allowing one out of many electrical signals connected to the multiplexer to pass through at one time. The selected electrical signal is a sample which is transmitted to an A-to-D converter so that a digital signal is generated and passed to a communications port and then to a remote host device. A clock pulse increments the next address in the sample order list to the multiplexer to establish the next signal sample to be transmitted to the host device. At the host device, the original electrical signals may be reconstituted. For example, the electrical signals may be physiological signals derived from transducers associated with an EKG. The host device may be a remote EKG apparatus.

11 Claims, 2 Drawing Sheets

PORTABLE DATA ACQUISITION UNIT

DESCRIPTION

1. Technical Field

The invention relates to digital data acquisition from multiple sources, and in particular to a portable data acquisition terminal for sampling signals from a plurality of transducers.

2. Background Art

In cardiography and similar medical applications, it is common to use a plurality of transducers which are affixed to a patient for deriving signals indicative of physiological conditions and functions. Since there can be many sources of electrical signals, there is sometimes an overabundance of data for recording or transmission. One approach has been to record all channels of data. Another approach, used mainly in EKGs, has been to combine signals to derive other signals which can be interpreted by a trained observer.

In U.S. Pat. No. 4,883,064 R. J. Olson et al. disclose a system for gathering EKG data by sequentially monitoring each of at least three patient leads for a period of greater than 15 seconds. The collected data may be stored or communicated over telephone lines for translation and interpretation at a remote site by trained individuals. The apparatus seeks to reduce the number of leads which are monitored to three pairs of electrodes producing data which can be monitored and selected, such as by a manual switch.

In U.S. Pat. No. 3,757,778, M. H. Graham discloses a terminal block for a plurality of electrocardiograph leads. The terminal block combines some of the leads into a composite signal, but also transmits uncombined signals in a cable to a distant signal processing and recording apparatus.

Both of the above patents show the need to transmit physiological data derived from a plurality of transducers to a remote location. On the one hand, the patent to Olson et al. shows the need for being able to select desired leads for transmission of selected signals to a remote location. On the other hand, the patent to Graham et al. shows that a user at a remote location can manually select data from desired leads and he may select the order in which signals are processed.

An object of the invention was to derive a more efficient manner of allowing physiological data signals to be selected from a remote location in a variable manner.

Summary of Invention

The above object has been met with a data acquisition unit which features a sample order which is variable by signalling from a remote location for collecting data from transducers at a local site. The sample order is a list stored in a volatile memory in a local terminal, the list controlling a multiplexer. Signals from a plurality of input transducers are fed to the multiplexer and the multiplexer has an output which produces signal samples as directed by the sample order register.

The sample order register may be varied upon command from a remote computer communicating with the register through a communications port associated with the register. The output of the multiplexers is a signal responsive to the sample order. This signal is converted to a digital signal and fed back to the communications port for transmission to the remote cardiograph or computer over a communications channel. This channel is then a two-way channel, a receive sub-channel containing sample order commands and a transmit sub-channel containing outgoing data samples.

An advantage of the invention is that the port, sample order register and multiplexers may all be combined in a hand held terminal which may be used near a patient. The output wire may be connected to a remote cardiograph or similar apparatus which is distant from the patient. The sample order is programmed into the terminal by the cardiograph. The terminal sequences through the sample order on command. The communications channel may be a simple low bandwidth channel using cable, or the like, which transmits time division multiplex signal samples which may be reconstituted at the host cardiograph or computer into the originally measured signals. The sample order may be changed by command from the cardiograph.

BEST MODE FOR CARRYING OUT THE INVENTION

Figure 1:
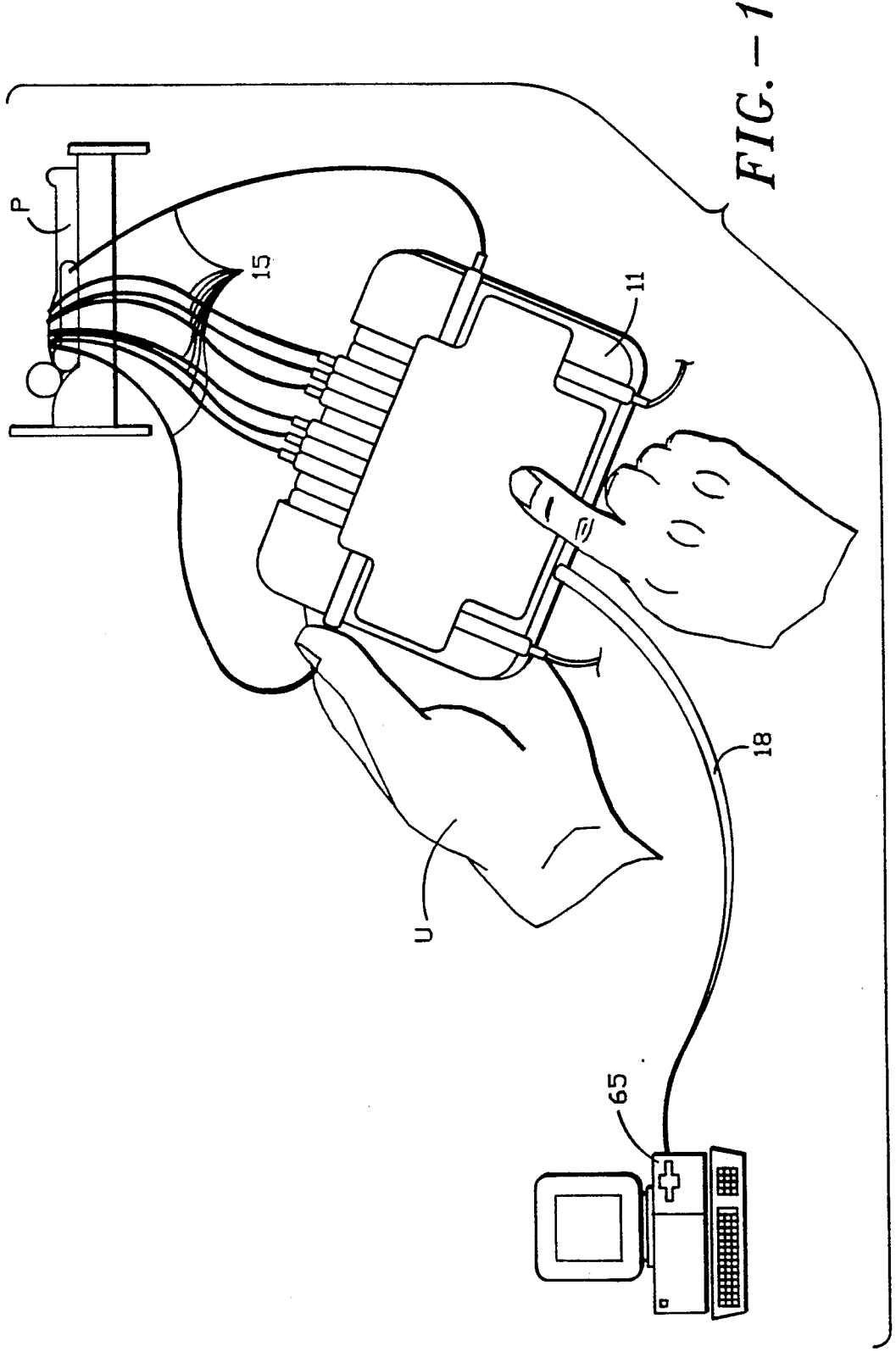
FIG. 1 is a plan perspective view of the portable data acquisition unit of the present invention.

With reference to FIG. 1, a portable data acquisition unit of the present invention features a terminal block 11 with a plurality of wire leads 15 extending to a patient P. Transducers are fixed to the patient for the purpose of gathering physiological data and converting the data to analog signals, such as skin potential. The transducers generate signals which are transmitted along the wire leads back to the terminal block 11. The terminal block contains a time division multiplexer which is controlled by a sample order register. The terminal output is a sample signal on cable 18 to a remote host device 65 which may be a computer or a cardiograph or similar device which also contains a CPU for communicating with the terminal block 11. Terminal block 11 is of a size which will readily fit in the hands of a user U and may have signal condition indicating features which are the subject of co-pending applications.

Figure 2:
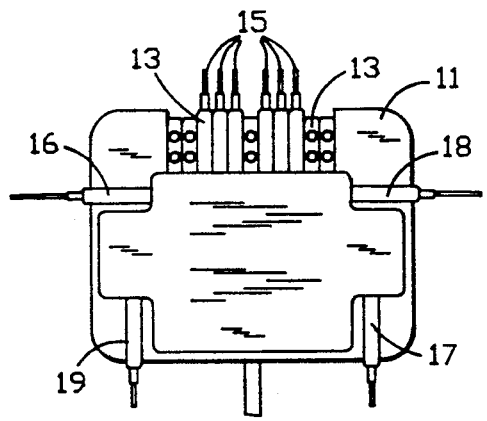
FIG. 2 is a top view of a data terminal used in the apparatus of FIG. 1.

In FIG. 2, the terminal block 11 is shown having a plurality of wire contacts 13 along the periphery of the terminal block. The wire contacts serve to terminate EKG lead wires 15. The wire contacts may be plugs or receptacles which receive corresponding jacks associated with the EKG lead wires. There are a total of fourteen wire contacts, including a right leg contact 19 and a left leg contact 17. Similarly, there is a right arm contact 16 as well as a left arm contact 18. The block is rectangular, having dimensions of approximately six inches on a side and a depth of about an inch and a half. Within the unit is a printed circuit board.

The electrical signals which are carried by wire leads 15 are analog signals which are derived from a plurality of transducers, such as electrodes which measure differences in electrical potential arising from contractions of the cardiac muscle. Alternatively, the leads could carry signals from acoustic, ultrasonic, pressure or almost any kind of electrical signal representing the measurement of a physical quantity. In other words, the data acquisition unit of the present invention is not restricted to use with EKGs, but may be used with any group of electrical signals to be transmitted to a remote location.

Figure 3:
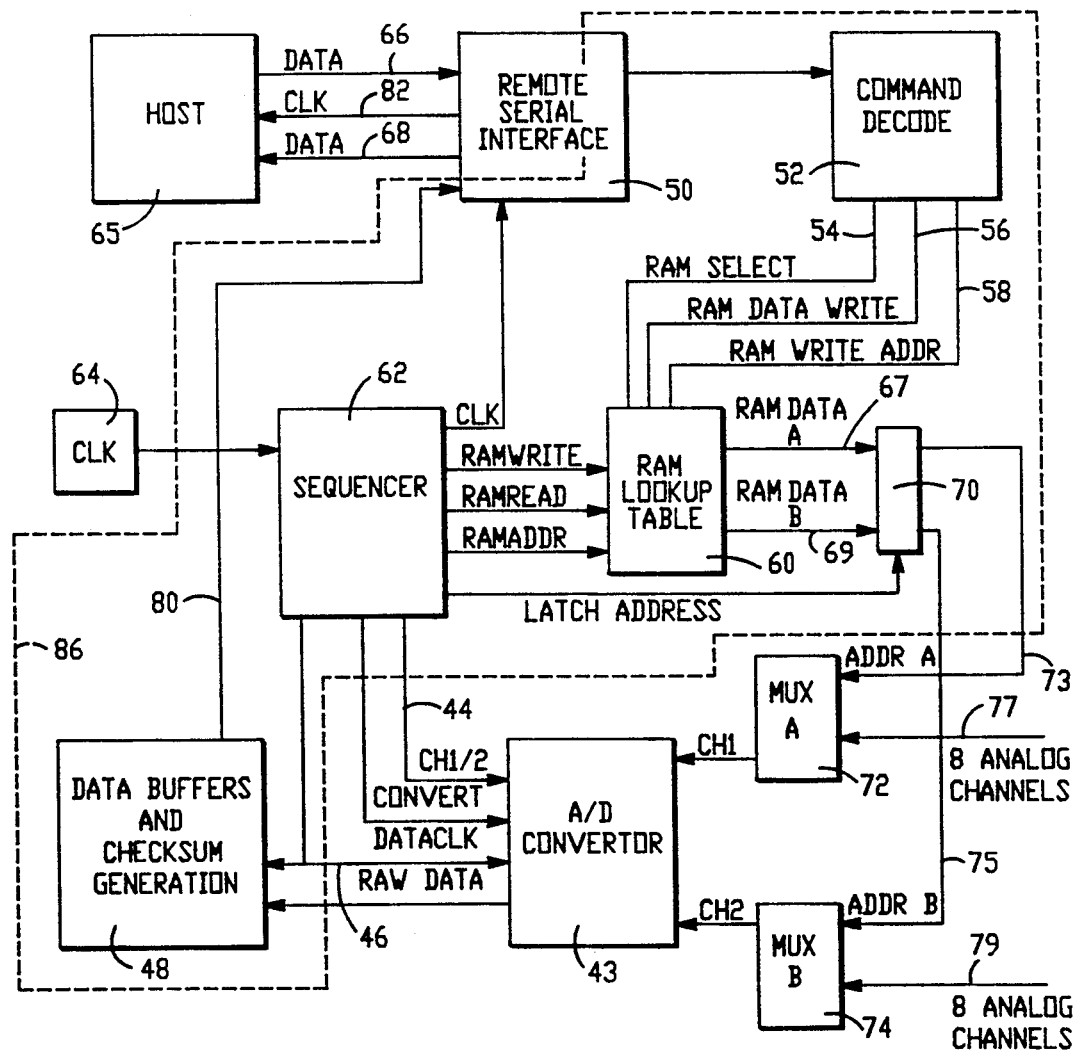
FIG. 3 is an electrical block diagram of the data terminal of FIG. 2.

With reference to the block diagram of FIG. 3, a sample order register 60 may be seen which is connected to receive an input from a communications port 66, 82, 68 while having an output to address logic 70. Preferably, the sample order register is a volatile memory, such as a random access memory or a barrel register. The register is of a size sufficient for holding a list containing the sample order. For example, if sixteen electrical leads are to be used, a possible sample order might be as follows: 10, 1, 16, 2, 3, 4, 5, 15, 7, 16, 6, 9, 8, 13, 14, 11. Alternatively, in many cases data from only a few leads might be required and the sample order might be as follows: 3, 5, 4, 6, 11, 12, 3, 5, 4, 6, 11, 12, 3, 5, 4, etc. In either case, sixteen numbers consisting of the sample order for sixteen wires are loaded into the sample order register.

On power up of the circuit, host device 65, typically a cardiograph, transmits a sample order to a remote terminal. The remote terminal consists of all the blocks in FIG. 3, except for host 65. Transmission of the sample order is initiated by the remote terminal. A bit in the terminal-to-host status word is used to verify that the sample order is set after power on. If not set, the host transmits the sample order. The status word is transmitted along data line 68 from the remote serial interface 50. The communications protocol is such that seventeen words are transmitted every 250 microseconds. There are sixteen data words, plus a word that contains the checksum of the previous sixteen data words, along with the status information.

The sample order signal is transmitted to the command decode logic block 52 where the information is broken into a RAM select signal, transmitted along line 54; a RAM data write signal, transmitted along line 56; a RAM write address signal, transmitted along line 58. All signals are transmitted to the RAM lookup table 60. The lookup table 60 provides output signals along lines 67 and 69, representing requests for analog data at specified multiplexers in accord with the sample order. A sequencer 62, driven by clock 64, provides an address to the lookup table 60 and latch 70 and at the appropriate time, latches the sample order data from latch 70 to multiplexers 72 and 74 via the multiplexer address lines 73 and 75. The command decode logic 52, RAM lookup table 60 and the sequencer 62 form a sample order register means. The sample order is a list of numbers, written at appropriate addresses corresponding to analog data signals to be selected from multiplexers. The multiplexers 72 and 74 each receive eight channels of analog data coming from transducers collecting physiological data. These channels are represented by lines 77 connected to multiplexer 72 and lines 79 connected to multiplexer 74. In response to control signals from a remote host, a sample order register means writes, holds and reads a number sequence to be used for sampling wire leads in multiplexers.

Signals from the multiplexers are transmitted to the A/D converter 43, which also receives the signal along line 44 for selecting between the two multiplexers. The logic signal for selecting the appropriate multiplexer is generated by sequencer 62 which is generating addresses for the RAM lookup table 60. Digital data from the transducers is transmitted along line 46 to data buffer 48 where data words and checksum signals are generated to form formatted data words using the protocol previously described. The formatted data words are transmitted along line 80 to the remote serial interface 50 for transmission to the host along line 68. A remote clock signal is also generated along line 82 for reading data at the host. There is bidirectional communication between the host and the remote terminal. The host may change the sample order at any time by providing a new list.

Since there are only sixteen analog channels, the same lead may be sampled multiple times within the 250 microsecond period of each data word transmitted to the host. This rapid sampling allows an increase in the usable signal bandwidth, as well as selection and variation among leads to be sampled.

Host computer 65, contained in a cardiograph, is similar to a personal computer of the 286 or 386 type. Analog-to-digital converter 43 and multiplexers 72 and 74 are commercial integrated circuits. The portion of the circuit within dashed line 86 is fabricated with a gate array, but could also be fabricated with discrete integrated circuits.

Since host device 65 establishes the sample order, the data acquisition unit which includes the sample order register is really a slave to the host device. This slave circuitry transmits whatever sample order is communicated from the host device. All of the functions indicated by the electrical blocks of FIG. 3 can be mounted on the small circuit card which fits into the data acquisition unit shown in FIG. 1.

We claim:

1. A data acquisition unit for receiving analog signals from transducers comprising,
    a portable terminal block terminating a plurality of wire leads for carrying analog signals from the transducers,
    a volatile sample order register means in said terminal block containing a sample order, the sample order listing a sequence for sampling said plurality of wire leads,
    a multiplexer in said terminal block having as an input said plurality of wire leads, each of the wire leads having an address, the multiplexer having an output,
    logic means in said terminal block connected between the sample order register means and the multiplexer for associating the sample order to particular wire leads,
    analog-to-digital converter means in said terminal block connected to the multiplexer for receiving the multiplexer output and providing a digital signal, and
    a communications port means in said terminal block connected to the analog-to-digital converter means for receiving the digital signal and providing an output signal onto a communications channel and for receiving a new sample order for the sample order register means.

2. This apparatus of claim 1 wherein said sample order register means comprises a random access memory adapted to contain the sample order and a sequencer which reads the sample order in sequence.

3. The apparatus of claim 2 wherein said sample order register means further comprises command decode logic.

4. The apparatus of claim 2 wherein said sequencer is connected to a clock.

5. The apparatus of claim 1 wherein said multiplexer comprises a pair of multiplexer devices.

6. The apparatus of claim 1 wherein said terminal block has hand-holdable size dimensions.

7. The apparatus of claim 1 wherein said communications port means is a serial port.

8. The apparatus of claim 1 wherein said communications channel is a two-way channel having send and receive sub-channels.

9. The apparatus of claim 8 wherein said receive sub-channel carries preselected sample order signals from a remote signal source.

10. A method of operating a data acquisition unit, comprising the steps of:
 providing a terminal with a number of wire lead inputs, transmitting a list of wire leads to be sampled in a particular sequence in the terminal from a remote location, the list having an order,
 outputting sampled signals from the terminal in accord with the order of the list, and
 changing the order of the list by providing a new list.

11. A data acquisition unit for providing to a host a series of digital signals, where each one of the digital signals corresponds to an analog signal present on a respective one of a plurality of wire leads, and where the series proceeds in a sequence selected by the host, the data acquisition unit comprising:

sample order register means for reading from the host a list of numbers representing the sequence, for storing the list of numbers, and for serially writing the numbers in the list, where each number in the list corresponds to one of the wire leads, the sample order register means including means for reading from the host a new list of numbers representing a new sequence;
 multiplexer means, receiving the numbers from the sample order register means, and having as inputs said plurality of wire leads, for, in response to receiving each number, providing as an output an analog signal corresponding to the analog signal present on the wire lead corresponding to the number;
 analog-to-digital converter means connected to the multiplexer means for receiving the output signal of the multiplexer means and outputting a corresponding digital signal; and
 communication port means connected to the output of the analog-to-digital converter means for receiving said digital signal and outputting said digital signal to said remote host.

* * * * *